US012678073B2

(12) United States Patent
Danielescu et al.

(10) Patent No.: US 12,678,073 B2
(45) Date of Patent: Jul. 14, 2026

(54) WEARABLE PHYSIOLOGICAL CHARACTERISTIC MONITORING DEVICE

(71) Applicant: Accenture Global Solutions Limited, Dublin (IE)

(72) Inventors: Lavinia Andreea Danielescu, Seattle, WA (US); Luke Fabrice Gockowski, Oakland, CA (US); Eric Michael Gallo, Moretown, VT (US); Jung Wook Park, Foster City, CA (US); Wade Ingram, Berkeley, CA (US)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 260 days.

(21) Appl. No.: 18/675,752

(22) Filed: May 28, 2024

(65) Prior Publication Data

US 2025/0366740 A1     Dec. 4, 2025

(51) Int. Cl.
| | |
|---|---|
| *A61B 5/145* | (2006.01) |
| *A61B 5/00* | (2006.01) |
| *A61B 5/1486* | (2006.01) |
| *A61L 31/02* | (2006.01) |
| *A61L 31/04* | (2006.01) |
| *H05K 3/22* | (2006.01) |

(52) U.S. Cl.
CPC ........ *A61B 5/14532* (2013.01); *A61B 5/1486* (2013.01); *A61B 5/6833* (2013.01); *A61B 5/742* (2013.01); *A61L 31/024* (2013.01); *A61L 31/042* (2013.01); *H05K 3/22* (2013.01); *A61B 2562/12* (2013.01); *A61L 2420/02* (2013.01)

(58) Field of Classification Search
CPC . A61B 5/14532; A61B 5/1486; A61B 5/6833; A61B 5/742; A61B 2562/12; A61L 31/024; A61L 31/042; A61L 2420/02; H05K 3/22
See application file for complete search history.

(56) References Cited

U.S. PATENT DOCUMENTS

2022/0267153 A1* 8/2022 Tour ...................... H01M 4/583

FOREIGN PATENT DOCUMENTS

| | | | | | | |
|---|---|---|---|---|---|---|
| CN | | 110423371 A | * | 11/2019 | ................ | C08J 5/18 |
| CN | | 114560460 A | * | 5/2022 | ........... | C01B 32/184 |
| WO | WO-2025057162 A1 | | * | 3/2025 | ............ | H01M 4/386 |

OTHER PUBLICATIONS

Ma, Zhiqiang, and Bee Luan Khoo. "Recent advances in laser-induced-graphene-based soft skin electronics for intelligent healthcare." Soft Science 4.3 (2024): N-A. (Year: 2024).*

* cited by examiner

*Primary Examiner* — Eric J Messersmith
(74) *Attorney, Agent, or Firm* — Mannava & Kang, P. C.

(57) ABSTRACT

Implementations of a wearable physical characteristic monitoring (PCM) device can include a substrate including two or more electrical traces, the two or more electrical traces being formed as laser-induced graphene (LIG) in a starch-based material layer, a sensor that provides a signal responsive to physiological characteristics of a patient wearing the PCM device, a processing system that provides physiological characteristics data based on the signal, and a communications system that enables communication of the physiological characteristics data from the PCM device, wherein the two or more electrical traces connect one or more of the sensor, the processing system, and the communications system.

22 Claims, 8 Drawing Sheets

WEARABLE PHYSIOLOGICAL CHARACTERISTIC MONITORING DEVICE

BACKGROUND

Certain disease conditions benefit from continuous or periodic monitoring of physiological characteristics. For example, diabetes is a medical condition, in which the body (e.g., human body) generates insufficient insulin (Type 1, insulin-dependent) or ineffective insulin (Type 2, not insulin-dependent). This can result in a patient going into a diabetic state that can result in a range of health-sensitive problems (e.g., seizure, kidney failure, skin ulcers). Patients can take proactive measures to prevent the onset of a diabetic state. For example, patients can take insulin injections and/or adjust their food/drink intake. However, to know when to take which proactive measures, the patient needs to be aware of their physiological state. In the context of diabetes, the physiological state includes blood glucose levels. In view of this, patients suffering from diabetes can use blood glucose monitors (BGMs) that measure the patient's blood glucose levels. Some BGMs are continuous in that they monitor the blood glucose level at regular intervals throughout a period of time (e.g., 24 hours, 48 hours, 72 hours). As such, the continuous BGM, which can be referred to as a continuous glucose monitor (CGM), is worn (attached to) the patient for the period of time.

CGMs, however, suffer from various drawbacks. For example, CGMs can be bulky resulting in discomfort over periods of time, as well as inadvertent detachment of the CGM from the patient. As another example, CGMs require an attachment means for attachment to the skin of the patient. Here, medical adhesives have been implemented. However, medical adhesives, particularly over extended periods of time, can be irritating to the patient's skin, some patients having allergic reactions to some medical adhesives. As still another example, CGMs need be periodically replaced. However, traditional CGMs can be relatively complex and expensive to produce. Further, traditional CGMs are not degradable and can end up as waste in landfills. Although take-back programs for disassembly and recycling can be implemented, getting users to participate in such take back programs is challenging.

SUMMARY

Implementations of the present disclosure are generally directed to wearable devices for monitoring physiological characteristics. More particularly, implementations of the present disclosure are directed to a wearable physiological characteristic monitoring (PCM) device that has a relatively thin profile, is made from hypoallergenic materials, and is less complex and more efficient to manufacture relative to traditional wearable PCM devices.

In some implementations, the wearable PCM device includes a substrate including two or more electrical traces, the two or more electrical traces being formed as laser-induced graphene (LIG) in a starch-based material layer, a sensor that provides a signal responsive to physiological characteristics of a patient wearing the PCM device, a processing system that provides physiological characteristics data based on the signal, and a communications system that enables communication of the physiological characteristics data from the PCM device, wherein the two or more electrical traces connect one or more of the sensor, the processing system, and the communications system. Other implementations of this aspect include corresponding systems, apparatus, and computer programs, configured to perform the actions of the methods, encoded on computer storage devices.

These and other implementations can each optionally include one or more of the following features: a hydrophobic layer formed on the substrate, the hydrophobic layer including hydrophobic graphene; the hydrophobic graphene is formed as LIG; further including an adhesive layer including an adhesive that is free from allergens including colophony (rosin), balsam of Peru (3.9%), 2-hydroxyethyl methacrylate, and carba mix; the adhesive is a starch-based adhesive; the communications system includes an electrochromic display; the electrochromic display is configured to selectively display a machine-readable code that encodes at least a portion of the physiological data; further including an energy harvesting unit to harvest energy to power the PCM device, the energy harvesting unit including one or more of an abiotic energy harvesting unit and a biotic energy harvesting unit; at least one of the two or more electrical traces is serpentine; the PCM is less than or equal to 1 mm thick; the substrate includes a biodegradable material the is coated with the starch-based material layer, the biodegradable material including one or more of bamboo, lignin, chitosan, and cellulose; and one or more components are one of biodegradable and recyclable.

In some implementations, a process for manufacturing a PCM device includes providing a substrate being composed of a starch-based material, forming two or more electrical traces as laser-induced graphene (LIG) in the substrate, mounting a set of electrical components for electrical communication between two of the two or more electrical traces: a first electrical component including a sensor that provides a signal responsive to physiological characteristics of a patient wearing the PCM device, and a second electrical component including a communication device to communicate physiological characteristics data from the PCM device, applying a starch-based layer to the substrate to cover the two or more electrical traces and one or more electrical components in the set of electrical components, and curing the starch-based layer to combine the starch-based layer and the substrate. Other implementations of this aspect include corresponding systems, apparatus, and computer programs, configured to perform the actions of the methods, encoded on computer storage devices.

These and other implementations can each optionally include one or more of the following features: further including forming a hydrophobic layer on the substrate, the hydrophobic layer including hydrophobic graphene; the hydrophobic graphene-rich traces are formed as LIG; further including applying an adhesive layer to the substrate, the adhesive layer including an adhesive that is free from allergens including colophony (rosin), balsam of Peru (3.9%), 2-hydroxyethyl methacrylate, and carba mix; the adhesive is a starch-based adhesive; the second electrical component includes an electrochromic display; the electrochromic display is configured to selectively display a machine-readable code that encodes at least a portion of the physiological data; a third electrical component in the set of electrical components includes an energy harvesting unit to harvest energy to power the PCM device, the energy harvesting unit including one or more of an abiotic energy harvesting unit and a biotic energy harvesting unit; at least one of the two or more electrical traces is serpentine; and the PCM is less than or equal to 1 mm thick.

The present disclosure also provides a computer-readable storage medium coupled to one or more processors and having instructions stored thereon which, when executed by the one or more processors, cause the one or more processors to perform operations in accordance with implementations of the methods provided herein.

The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

It is appreciated that methods in accordance with the present disclosure can include any combination of the aspects and features described herein. That is, for example, apparatus and methods in accordance with the present disclosure are not limited to the combinations of aspects and features specifically described herein, but also may include any combination of the aspects and features provided.

The details of one or more implementations of the present disclosure are set forth in the accompanying drawings and the description below. Other features and advantages of the present disclosure will be apparent from the description, drawings, and claims.

BRIEF DESCRIPTION OF DRAWINGS

Like reference numbers and designations in the various drawings indicate like elements.

DETAILED DESCRIPTION

Figure 1:
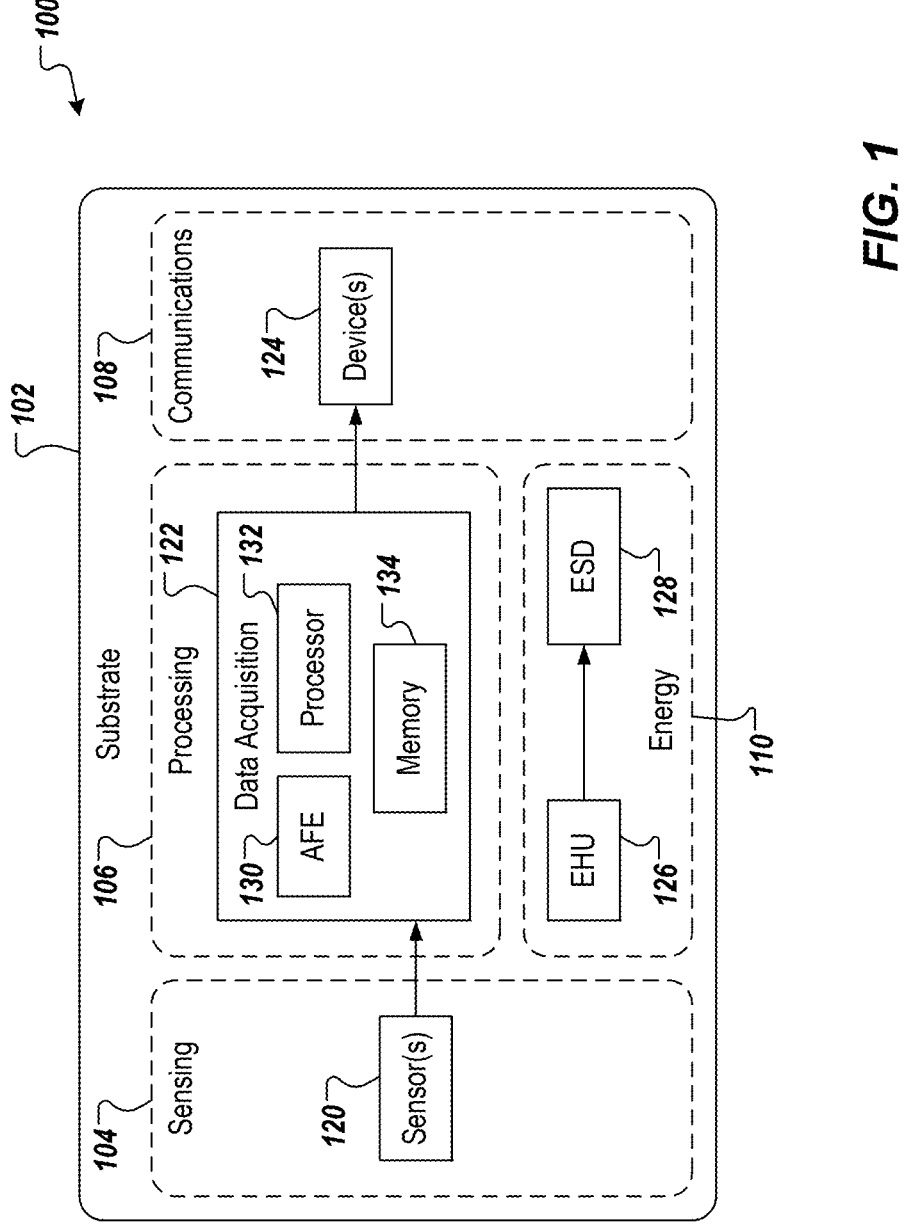
FIG. 1 depicts a block diagram of an example physiological characteristic monitoring (PCM) device in accordance with implementations of the present disclosure.

Implementations of the present disclosure are generally directed to wearable devices for monitoring physiological characteristics. More particularly, implementations of the present disclosure are directed to a wearable physiological characteristic monitoring (PCM) device that has a relatively thin profile, is made from materials that are less likely to cause allergic reactions, and is less complex and more efficient to manufacture relative to traditional wearable PCM devices.

In some implementations, a wearable PCM device includes a substrate including two or more electrical traces, the two or more electrical traces being formed as laser-induced graphene (LIG) in a starch-based material layer, a sensor that provides a signal responsive to physiological characteristics of a patient wearing the PCM device, a processing system that provides physiological characteristics data based on the signal, and a communications system that enables communication of the physiological characteristics data from the PCM device, wherein the two or more electrical traces connect one or more of the sensor, the processing system, and the communications system.

In some implementations, a process for manufacturing a PCM device includes providing a substrate being composed of a starch-based material, forming two or more electrical traces as laser-induced graphene (LIG) in the substrate, mounting a set of electrical components for electrical communication between two of the two or more electrical traces: a first electrical component including a sensor that provides a signal responsive to physiological characteristics of a patient wearing the PCM device, and a second electrical component including a communication device to communicate physiological characteristics data from the PCM device, applying a starch-based layer to the substrate to cover the two or more electrical traces and one or more electrical components in the set of electrical components, and curing the starch-based layer to combine the starch-based layer and the substrate.

It is appreciated that PCMs can be used to monitor medical conditions as well as general wellness. For purposes of non-limiting illustration, monitoring of medical conditions is referenced herein. Implementations of the present disclosure are described in further detail herein with reference to an example medical condition, which includes diabetes that requires monitoring of blood glucose level (i.e., a physiological characteristic). It is contemplated, however, that implementations of the wearable device of the present disclosure can be realized for continuous monitoring of any appropriate physiological characteristic that may be relevant to any appropriate medical condition and/or general wellness (e.g., athletic performance, preventative care, skin temperature).

To provide further context for implementations of the present disclosure, and as introduced above, disease conditions, such as diabetes, can benefit from periodic or continuous monitoring of physiological characteristics. In the example context of diabetes, patients can take proactive measures to prevent onset of a diabetic state. For example, patients can take insulin injections and/or adjust their food/drink intake. However, to know when to take which proactive measures, the patient needs to be aware of their physiological state. In the context of diabetes, the physiological state includes blood glucose levels. In view of this, patients suffering from diabetes can use blood glucose monitors (BGMs) that measure the patient's blood glucose levels. Some BGMs are continuous in that they monitor the blood glucose level at regular intervals throughout a period of time (e.g., 24 hours, 48 hours, 72 hours). As such, the continuous BGM, which can be referred to as a continuous glucose monitor (CGM), is worn (attached to) the patient for the period of time.

PCM devices, such as CGMs, however, suffer from various drawbacks. For example, CGMs can be bulky (e.g., due to size, weight, thickness, etc. of components) resulting in discomfort over periods of time, as well as inadvertent detachment of the CGM from the patient. As another example, CGMs require an attachment means for attachment to the skin of the patient. Here, medical adhesives have been implemented. However, medical adhesives, particularly over extended periods of time, can be irritating to the patient's skin, some patients have allergic reactions to some medical adhesives. For example, allergic reactions to certain medical adhesives have been observed—including colophony (rosin), balsam of Peru (3.9%), 2-hydroxyethyl methacrylate, and carba mix (which includes, for example, diphenylguanidine, zincdibutyldithiocarbamate, and zincdiethyldithiocarbamate). As still another example, wearable CGMs need be periodically replaced. However, traditional wearable CGMs can be relatively complex and expensive to produce. Further, traditional CGMs are not degradable and can end up as waste in landfills. Although take-back programs for disassembly and recycling can be implemented, getting users to participate in such take back programs is challenging.

In view of this, implementations of the present disclosure provide improved wearable PCM devices, such as CGMs, and processes for manufacture thereof. As described in further detail herein, the PCM devices of the present disclosure are more patient-friendly, are of lower profile (e.g., lower geometric profile, thinner), are less complex, and are more cost-efficient than traditional PCM devices. Further, the PCM devices of the present disclosure consider end-of-life and include sustainable, degradable, and/or recyclable components. In some implementations, PCM devices of the present disclosure have an ultrathin form factor (e.g., a thickness of ≤1 mm), provide a flexible and wearable device architecture, and include skin-adhesives that are free of common dermatitis-inducing allergens (e.g., rosin, acrylates). For example, and in terms of form factor, PCM devices of the present disclosure can be more akin to adhesive bandages (e.g., Band-Aid® brand of adhesive bandages) than to traditional PCM devices (e.g., traditional CGMs). As described herein, processing, communication, energy storage, energy harvesting, and fabrication techniques to provide PCM devices of the present disclosure achieve the light, ultrathin form factor relative to traditional PCMs.

FIG. 1 depicts a block diagram of an example PCM device 100 in accordance with implementations of the present disclosure. In the example of FIG. 1, the PCM device 100 includes a substrate 102, a sensing system 104, a processing system 106, a communications system 108, and an energy system 110.

The sensing system 104 includes one or more sensors 120. An example sensor can include, without limitation, a glucose sensor that is responsive to glucose levels in blood. A glucose sensor can be described as an amperometric electrochemical biosensor that generates a current ($I_{glu}$) responsive to the electrochemical reaction between glucose and a glucose oxidase layer on an electrode. In some examples, glucose sensors can include non-enzymatic electrochemical reactions between glucose and inorganic catalysts on electrodes. It is contemplated, however, that the one or more sensors 120 can include any appropriate sensor.

The processing system 106 includes a data acquisition module 122 that receives signals from the one or more sensors 120 and processes the signals to determine and store data. In the example of FIG. 1, the data acquisition module 122 includes an analog front end (AFE) 130, a processor 132, and memory 134. In some examples, the AFE 130 includes analog signal conditioning circuitry to convert analog signals received from the one or more sensors 120 to digital signals that provide digital values. Example digital values can include current ($I_{glu}$) values. That is, the AFE 130 performs functionality of an analog-to-digital converter. In some examples, the AFE 130 performs one or more of signal conditioning (e.g., prior to digital conversion), such as amplifying and filtering signals (e.g., a current signal from a glucose sensor). In some examples, the AFE 130 can could also perform frequency filtering, compare the signal to a reference value and/or other analog operations. In some examples, the digital values are stored as sensor data in the memory 134. In some examples, the processor 132 processes the digital values to provide physiological characteristic values that can be stored in the memory 134 as physiological characteristic data. For example, the processor 132 can process the digital values to provide blood glucose values (e.g., converting the digital values to blood glucose values), which can be stored in the memory 134 as blood glucose data. In some examples, data stored in the memory 134 can have associated metadata. Example metadata can include, without limitation, a timestamp indicating a time at which the physiological characteristic data was generated.

In some examples, the memory 134 is provided as non-volatile memory. For example, the memory 134 can include readable-writable resistive random-access memory (RRAM) and/or electrically erasable programmable read-only memory (EEPROM). The memory 134 can include any appropriate type of memory. In some examples, memory can be embedded within the processor 132 or external to the processor 132. Read-only memory would contain the system operating instructions and key identification of the sensing system. Storage memory would record the sensor(s) output and other key operational parameters for reporting externally.

The communications system 108 includes one or more devices 124 for communicating information from the PCM device 100. Examples of the one or more devices 124 are discussed in further detail herein.

The energy system 110 provides power to components of one or more of the sensing system 104, the processing system 106, and the communications system 108. In the example of FIG. 1, the energy system includes an energy harvesting unit (EHU) 126 and an energy storage device (ESD) 128. In some examples, the PCM device 100 can be absent the EHU 126.

In some examples, the EHU 126 harvests energy for storage in the ESD 128. The EHU 126 can include any appropriate EHU or combinations thereof. Example EHUs can include, without limitation, abiotic EHUs and biotic EHUs. Example abiotic EHUs can include, without limitation, a solar-based EHU (e.g., solar panels to harvest solar energy, photovoltaics), a thermoelectric EHU (e.g., thermoelectric energy generation from heat emitted by a patient), a piezoelectric/triboelectric EHU to capture energy from motion and/or vibration (e.g., crystalline or semi-crystalline), and a radio frequency (RF) EHU (e.g., integrated antenna to receive energy from external source). Example biotic EHUs can include, without limitation, a microbial EHU (e.g., microbial fuel cells) and an enzymatic EHU (e.g. enzymatic biofuel cell to harvest energy from patient sweat).

The ESD 128 stores energy that is used to power components of one or more of the sensing system 104 (sensors of the sensing system 104), the processing system 106, and the communications system 108. The ESD 128 can include any appropriate ESD or combinations thereof. Example ESDs can include, without limitation, a battery, a capacitor, and/or a supercapacitor. For example, the PCM device 100 can be powered by an ESD that includes a flexible lithium polymer (LiPo) battery, a zinc-ion battery (ZIB), and/or a MXene-based flexible supercapacitor, each of which can be manufactured to be relatively thin, flexible, and stretchable.

In accordance with implementations of the present disclosure, the substrate 102 includes an adhesive layer that enables the PCM device 100 to be removably attached to skin of a user (cutaneous adherence). The adhesive layer includes an adhesive compound that is non-irritating to the skin for a broad and diverse population of people. As such, the adhesive is free of allergens including, but not limited to, colophony (rosin), balsam of Peru (3.9%), 2-hydroxyethyl methacrylate, and carba mix (which includes, for example, diphenylguanidine, zincdibutyldithiocarbamate, and zincdiethyldithiocarbamate).

In some implementations, the adhesive is a starch-based adhesive. Starch is one of the most abundant natural polymers on Earth and is found in high quantities in staple foods such as potatoes and rice. Starch-based materials have been explored extensively for wound-dressing materials as well as for transient, flexible electronics. Example starch-based materials can include, without limitation, starch-based nanofibrous scaffolds. Other examples of starch-based materials include biodegradable packaging, foams, and films—all of which typically use wheat, corn, rice, and/or potato derivatives.

In some examples, the starch-based material also functions as a precursor material for forming electrically conductive pathways in and/or on the substrate 102. For example, electrically conductive pathways can be formed using laser-induced graphene (LIG), which can be described as a carbon-based nanomaterial that can be fabricated on a wide range of carbonaceous materials, such as starch-based materials. LIG can be formed without using any additional chemicals or other compounds. LIG has properties including, but not limited to, high surface area, good electrical conductivity, good thermal conductivity, environmental-friendliness, easy fabrication, and patternability. Further, LIG can be formed on starch and cellulose achieving good electrical conductance (e.g., $\leq 5\Omega/sq$). In some examples, by tuning the atmosphere of lasing, the LIG can be tuned from superhydrophobic (i.e., extremely liquid-repellent) to super-hydrophilic (i.e., extremely liquid-attractant). In view of this, implementations of the present disclosure include spatially varying hydrophobicity and conductivity across the substrate 102. That is, for example, hydrophobic properties and/or conductive properties of the substrate 102 can vary across the substrate 102.

It can be further noted that, being formed of starch-based materials, the substrate 102 is compostable. As such, the PCM device 100 can be described as sustainable and environmentally friendly. For example, electrical components (e.g., of one or more of the sensing system 104, the processing system 106, the communications system 108, and the energy system 110) can be detached from the substrate 102, and the substrate 102 can be composted. Some or all of the electrical components can be recycled.

It can be noted that the adhesive and/or substrate can be provided using any number of compatible sustainable materials, such as bamboo fibers, chitosan, lignin or cellulose materials. In some implementations, the adhesive and/or the substrate 102 can be provided using biodegradable gelatin methacryloyl (GelMA) aerogels. GelMA has been used widely in bioprinting, implants, tissue engineering, and slight modifications to the chemical process makes this material flexible and suitable for use in wearable devices, such as PCMs.

FIGS. 2A-2D depict respective example PCM devices in accordance with implementations of the present disclosure.

Figure 2A:
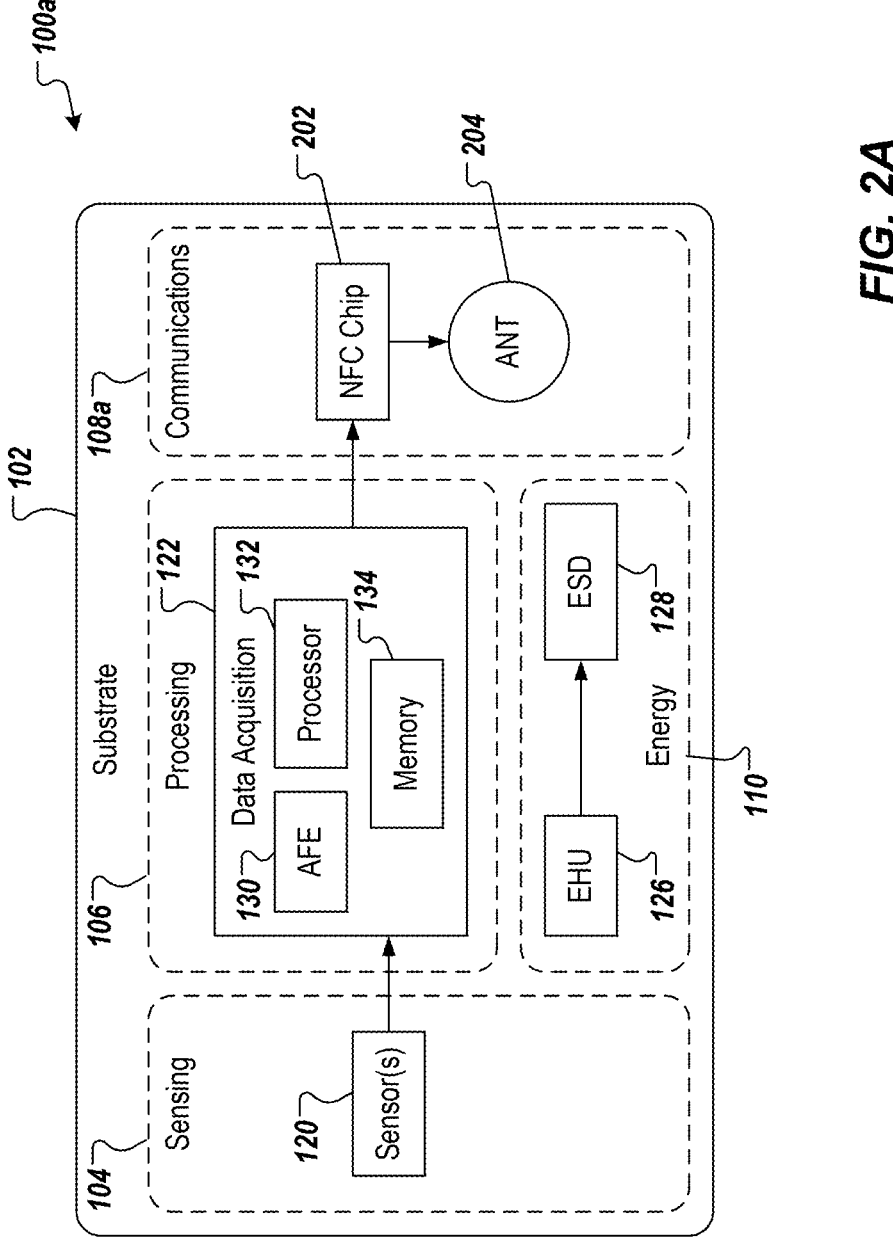
FIGS. 2A-2D depict respective example PCM devices in accordance with implementations of the present disclosure.

With particular reference to FIG. 2A, a PCM device 100a is depicted and includes the substrate 102, the sensing system 104, the processing system 106, a communications system 108a, and the energy system 110. In the example of FIG. 2A, the communications system 108a is provided as a near-field communication (NFC) system and includes an NFC chip 202 and an antenna 204. In some examples, the NFC chip 202 and/or the antenna 206 can be fabricated using LIG, as discussed herein. In some examples, the PCM device 100a can be prompted to broadcast physiological characteristic data to an external device (e.g., a smartphone). In this manner, the physiological characteristic data can be recorded in and displayed on the external device. Although NFC is discussed, it is contemplated that other technologies, such as passive radio frequency (RF) can be used. More generally, any appropriate communication protocol and components can be implemented.

Figure 2B:
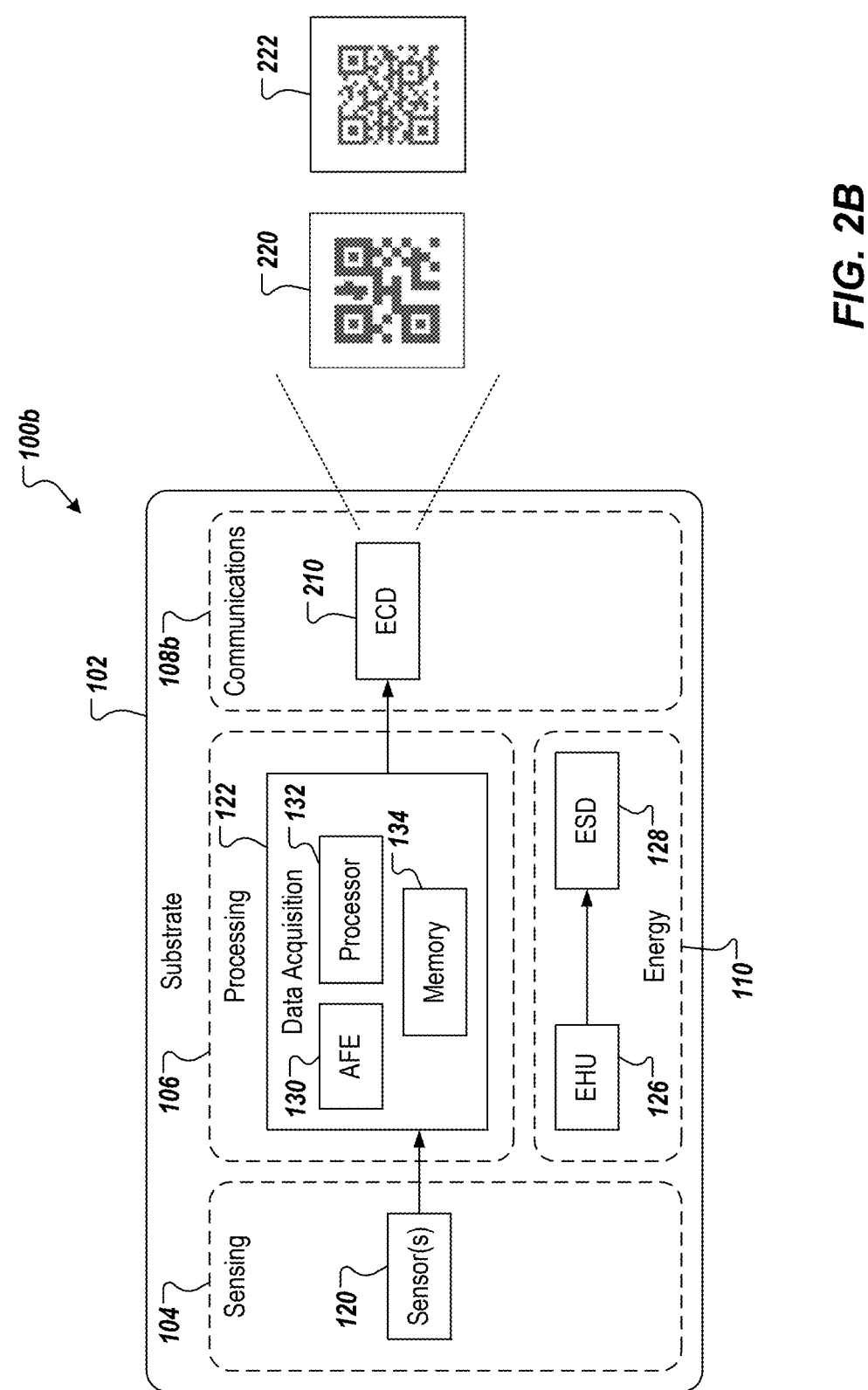

With particular reference to FIG. 2B, a PCM device 100b is depicted and includes the substrate 102, the sensing system 104, the processing system 106, a communications system 108b, and the energy system 110. In the example of FIG. 2B, the communications system 108b is provided as a display system and includes an electrochemical display (ECD) 210. In some examples, the PCM device 100b can be prompted to generate an image on the ECD 210 that depicts physiological characteristic data. In this manner, the physiological characteristic data can be viewed by a user. In some examples, the ECD 210 can display an image of a machine-readable code that encodes physiological characteristic data. Example machine-readable codes include, without limitation, bar codes and quick response (QR) codes. In some examples, an external device (e.g., a smartphone) can scan the machine-readable code to decode the physiological characteristic data and display physiological characteristic data. In some examples, the machine-readable code is visibly displayed, such that a human is able to see the machine-readable code. In some examples, the machine-readable code is not visible to humans (e.g., is displayed as an infrared image or near infrared (NIR) image). In such examples, the machine-readable code can only be read by an external device (e.g., smartphone) having an infrared (or NIR) imager.

With regard to encoding physiological characteristic data, blood glucose levels rarely fall outside the bounds of 60-200 mg/dL. As such, each measurement of blood glucose can be stored as a byte of data (physiological characteristic data). Furthermore, commercially-available continuous glucose meters only offer integer (not floating point) precision. With regard to QR codes, in particular, a QR code can store up to 2953 bytes of data. At a glucose sampling rate of once per minute (or 1440 times per day), approximately 1440 bytes of data is generated per day. As such, a QR code can store up to two full days of glucose monitoring data.

In some examples, the machine-readable code can refresh over time to encode physiological characteristic data as it is recorded. This is represented in FIG. 2B, depicting a first QR code 220 at a first time ($t_1$) and a second QR code 222 at a second time ($t_2$), the second QR code 222 encoding more physiological characteristic data than the first QR code 220.

The ECD 210 provides the PCM device 100b with a tattoo-like appearance on the user. For example, the ECD 210 can display customizable content for multiple purposes including, but not limited to, aesthetics, user personalization, and advertising.

Figure 2C:
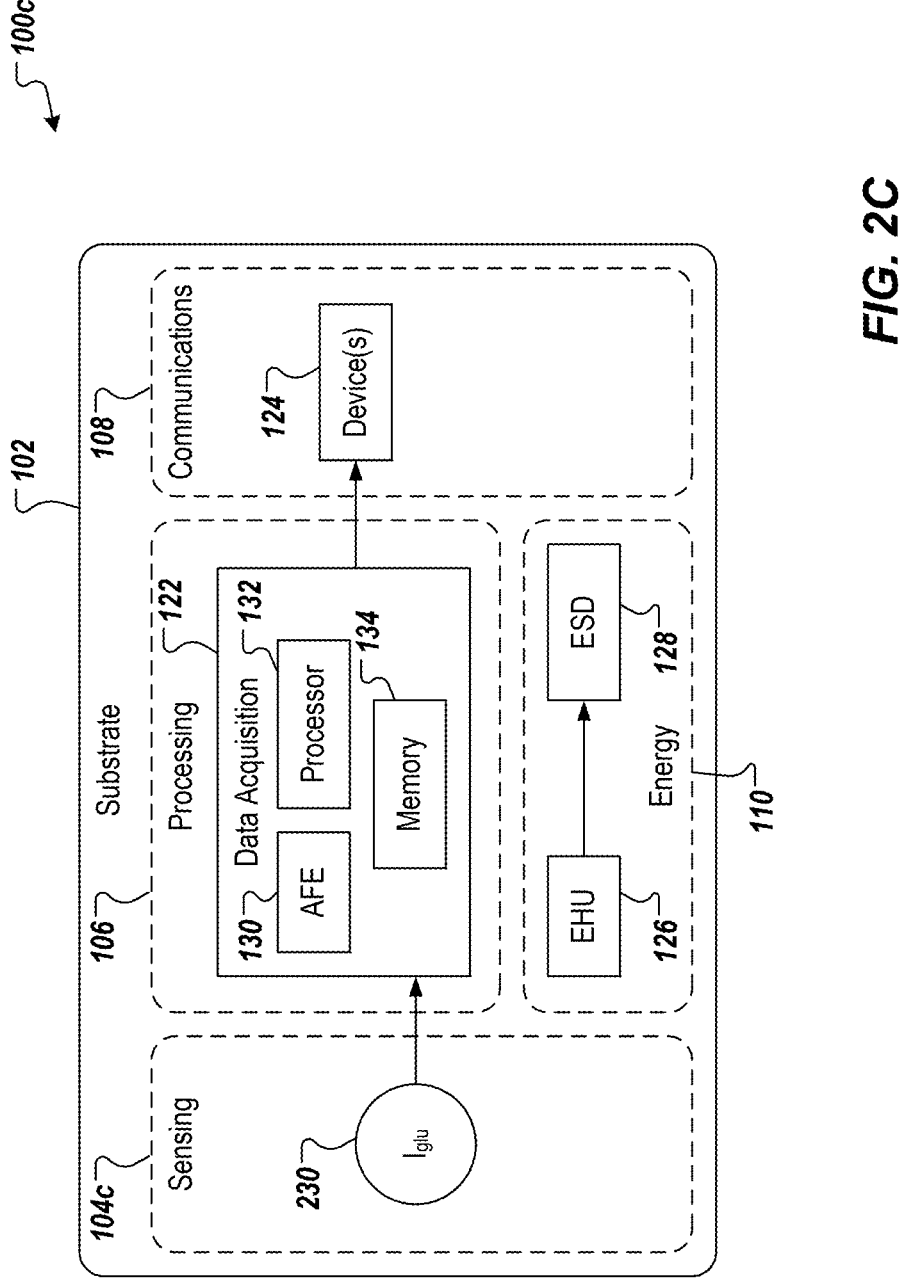

With particular reference to FIG. 2C, a PCM device 100c is depicted and includes the substrate 102, a sensing system 104c, the processing system 106, the communications system 108, and the energy system 110. In the example of FIG. 2C, the sensing system 104c includes a blood glucose sensor 230.

In some examples, the blood glucose sensor 230 includes a probe that is inserted beneath the surface of the skin (sub-cutaneous), where glucose sampled in the interstitial fluid can be measured. In some examples, the blood glucose sensor 230 can be biodegradable or bioabsorbable. In some examples, the probe leverages a glucose-enzyme reaction that is detected by an amperometric sensor. The sensor electrode can be decorated with a glucose oxidase (GOx) enzyme, whose oxidation-reduction (redox) reaction with glucose generates a current ($I_{glu}$) in the electrode. More particularly, the (GOx) enzyme is used to convert glucose into gluconic acid and hydrogen peroxide. The hydrogen peroxide can be oxidized, which produces electrons that are proportional to the glucose concentration. The flow of the electrons produces the current ($I_{glu}$) that can be measured (i.e., amperometric sensing). However, the current ($I_{glu}$) can be a relatively small, weak signal. In view of this, current signals are processed in the AFE 130, which can include amplifiers, filters, and the like to produce an accurate and precise digital signal.

In some examples, the blood glucose sensor 230 is a sweat-based glucose sensor that generates a current ($I_{glu}$) responsive to glucose levels in sweat of a patient. Sweat contains a number of analytes (e.g., ammonia, ethanol, lactate, urea) that provide indications of the physiological state of a patient. Sweat also contains glucose, which can be sensed using non-invasive sensors, which interact with the surface of the skin instead of puncturing the skin or drawing blood. In some examples, the sweat-based glucose sensor can be created using LIG. For example, graphene foams can be soaked in a solution of enzyme and phosphate-buffered saline (PBS) to produce robust electrode and cathodes for a biofuel cell. Glucose oxidase plays an important role in the body converting glucose into a form that cells can use, such as adenosine triphosphate (ATP) molecules. During this process (known as glycolysis), electrons are freed in the oxidation of glucose. These electrons eventually pass to oxygen available in the blood where it is reduced to $H_2O$.

In sweat-based glucose sensing, the electron pathway can be simplified after the oxidation of glucose at the anode. The current generated by the oxidation of glucose can be correlated to the concentration of glucose in the media (e.g., sweat) that the sensor is touching. Sustainable materials can be used in the fabrication of the anode and cathode. In this manner, at least portions of the PCM device 100 can safely biodegrade in a landfill or compost. For example, and without limitation, cotton can be used for a biofuel cell, the cotton being modified with gold nanoparticles (Au NPs), poly(ethylenimine) (PEI), GOx, and tris-(2-aminoethyl) amine, a small molecule that can covalently bond with Au NPs and link to the GOx and efficiently shuttle electrons. Further, devices for glucose sensing and biofuel cells can be provided using chitosan and graphene with glucose oxidase immobilized on the surface. A sensitivity down to a 0.02 mM detection limit has been shown.

In some examples, the blood glucose sensor 230 is an odor-based glucose sensor that generates a current ($I_{glu}$) responsive to glucose levels correlated with volatiles emitted by the body, such as isoprene, a byproduct produced when glucose levels are very low. In some examples, sensing can include using neurons to detect volatiles. For example, synthetic biotechnology can be incorporated to sense and detect volatile compounds using neurons and proteins to signal when a small molecule interacts with the sensing capability of the neuron.

Figure 2D:
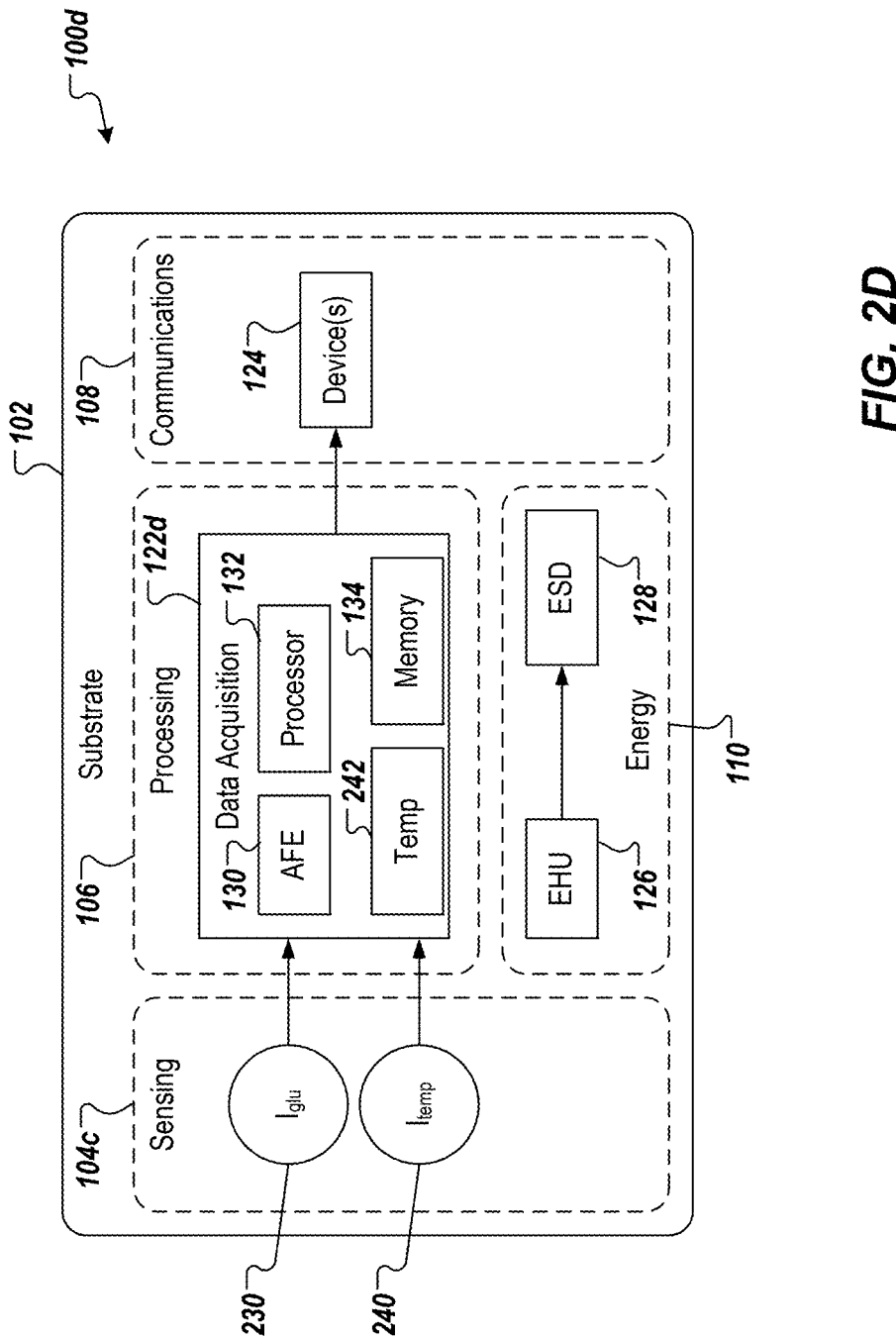

With particular reference to FIG. 2D, a PCM device 100d is depicted and includes the substrate 102, a sensing system 104d, a processing system 106d, the communications system 108, and the energy system 110. In the example of FIG. 2D, the sensing system 104d includes the blood glucose sensor 230 and a temperature sensor 240 that generates a current ($I_{temp}$) responsive to a temperature of the patient. The processing system 106d includes a data acquisition unit 122d that includes a temperature module 242 to provide temperature data based on a signal from the temperature sensor 240. The temperature data can be stored in the memory and can be communicated through the one or more devices 124 of the communications system 108, as described herein. In some examples, the temperature data can be used to correct measurements and/or ensure accurate data by accounting for temperature affecting analog signals read by other peripheral components.

Figures 3A, 3B:
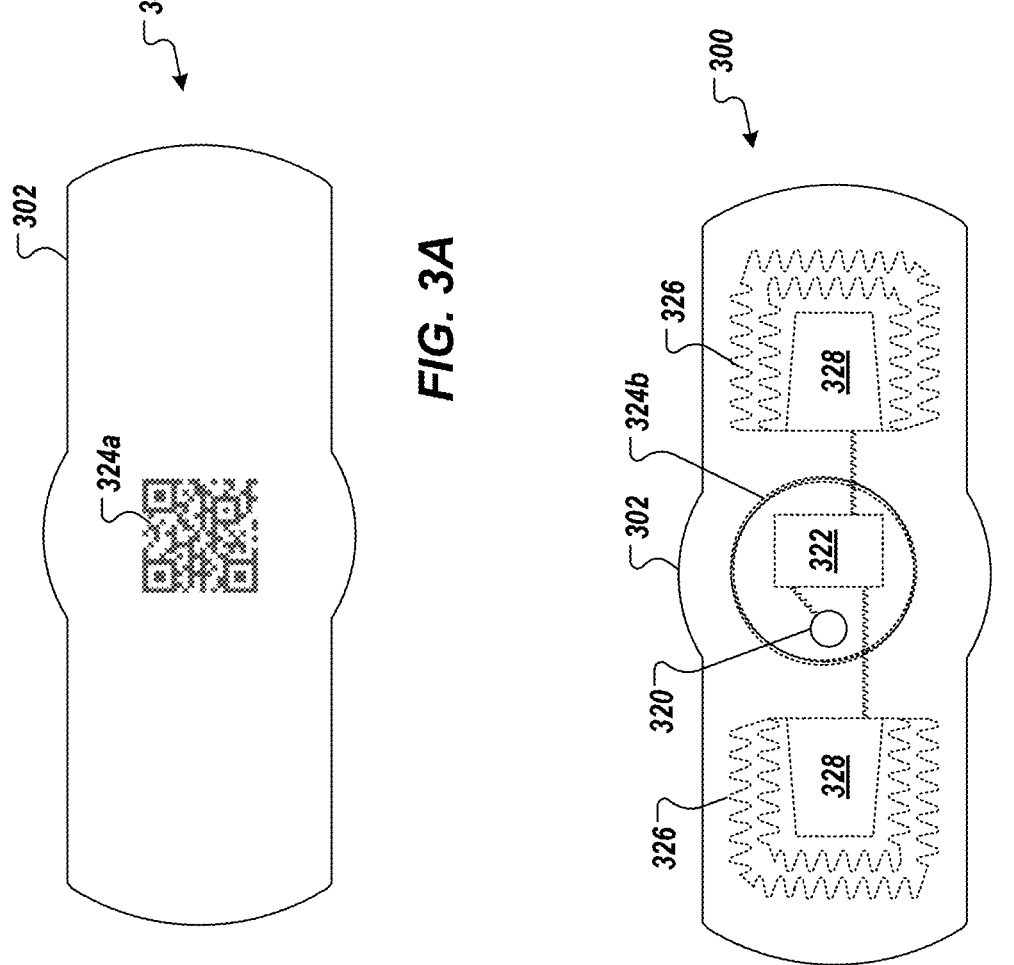
FIGS. 3A and 3B depict an example PCM device in accordance with implementations of the present disclosure.

FIGS. 3A and 3B depict an example PCM device 300 in accordance with implementations of the present disclosure. Although each is not explicitly and entirely depicted in FIGS. 3A and 3B, the PCM device 300 includes a sensing system, a processing system, a communications system, and an energy system, such as described herein with reference to FIGS. 1-2D. In the example of FIGS. 3A and 3B, the PCM device 300 includes a substrate 302 (starch-based and/or other appropriate materials), a sensor 320, a data acquisition module 322, devices 324a, 324b, EHUs 326, and ESDs 328. The device 324a includes an ECD (e.g., that includes a biodegradable substrate) that can display images, such as a machine-readable code, to communicate physiological data and/or aesthetic images. The device 324b includes an NFC device that can be used to communicate physiological data. While the example of FIGS. 3A and 3B depict both devices 324a, 324b, the PCM 300 can include only one of the devices 324a, 324b and/or can include another device for communicating physiological data. In some examples, the EHUs 326 include thermoelectric EHUs.

As depicted in FIG. 3B, electrical traces (e.g., laser-induced graphene-rich traces) can be formed as serpentine interconnects. For example, human skin can strain up to ~20%. To account for this stretchability, serpentine interconnects enable the electrical traces to stretch/deform without damage or adverse effect to electrical conductance. The winding of the electrical traces enables stretchability of up to, for example, 300%.

Figure 4A:
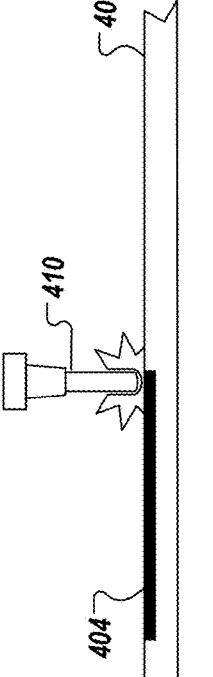
FIGS. 4A-4F depicts an example process for manufacturing a PCM device in accordance with implementations of the present disclosure.
Figure 4B:
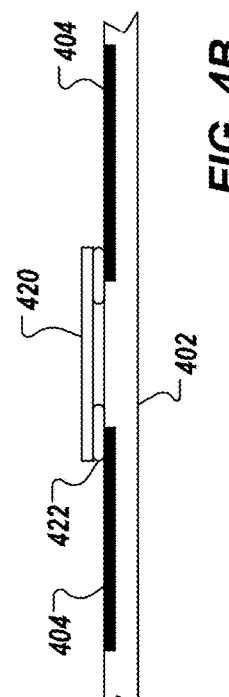

FIGS. 4A-4F depicts an example process for creating a PCM device in accordance with implementations of the present disclosure. With reference to FIG. 4A, a starch-based substrate 402 is provided and a laser 410 is used to form graphene-rich traces 404 (LIG) in the substrate 402. In some examples, the laser 410 is set to a relatively low fluence (e.g., 3-60 J cm$^{-2}$, correlating roughly to powers of 2-18 W and speeds of 10-72 cm s$^{-1}$ used in combination) to form the graphene. In some examples, the fluence of the laser 410 can be increased (e.g., >70 J cm–2, correlating for example to a power of 55 W and speeds of 10 cm s$^{-1}$ used in combination) to cut the substrate 402 to a desired shape. In accordance with implementations of the present disclosure, the graphene 404 can be formed in the substrate (or other coatings) to define conductive electrical traces. With reference to FIG. 4B, electrical components 420 can be mounted to the substrate using an electrically conductive adhesive 422. For example, the electrically conductive adhesive 422 can be used to adhere an electrical component to the graphene 404 and/or the substrate 402.

Figure 4C:
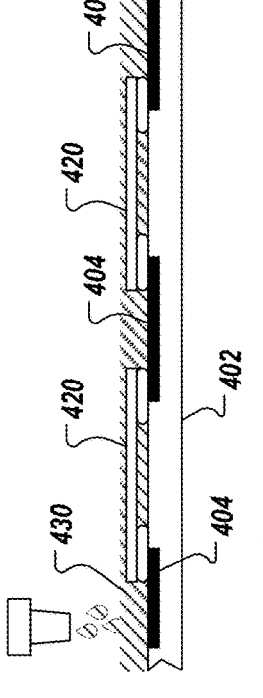
Figure 4D:
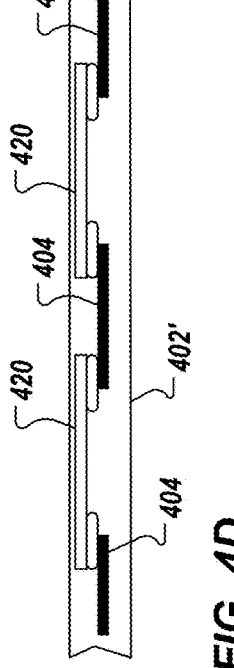
Figure 4F:
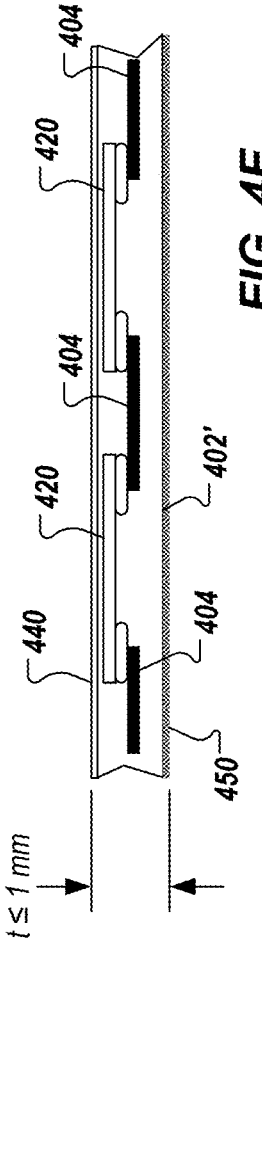
Figure 4E:
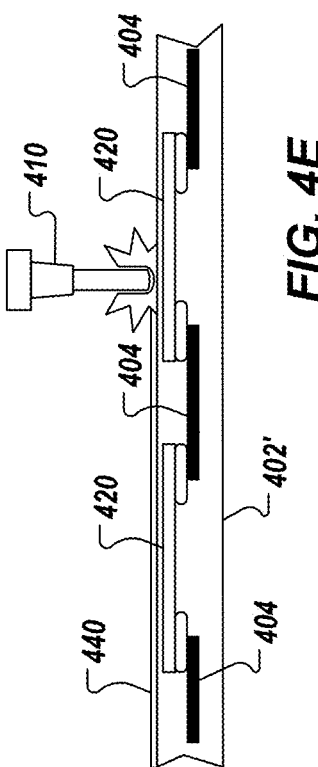

With reference to FIGS. 4C and 4D, a spin-coated layer 430 is applied to encapsulate the graphene 404 and the electrical components 422. Curing (e.g., by baking) can be used to solidify the layer 430 and to integrate the layer 430 with the substrate 402 as a single, continuous substrate 402'. With reference to FIG. 4E, the laser 410 can be used to form a graphene-rich layer 440 on the substrate 402'. In some examples, the graphene-rich layer 440 can be made hydrophobic to provide a liquid (e.g., water, sweat) repellent surface. In some examples, this is achieved by lasing under a nitrogen ($N_2$) atmosphere. In some examples, the graphene-rich layer 440 can be made omniphobic to provide a surface with more broadly repellant characteristics. With reference to FIG. 4F, an adhesive layer 450 is applied to a skin-facing surface of the substrate 402'. In some examples, the adhesive is starch-based and its adhesive properties are enhanced by sweat. As discussed herein, the adhesive layer 450 is free of allergens including, but not limited to, colophony (rosin), balsam of Peru (3.9%), 2-hydroxyethyl methacrylate, and carba mix (which includes, for example, diphenylguanidine, zincdibutyldithiocarbamate, and zincdiethyldithiocarbamate). In the example of FIG. 4F, the PCM device has a thickness (t) of less than or equal to 1 mm. In some examples, a thickness of the PCM device can vary between a minimum thickness and a maximum thickness. In some examples, the maximum thickness is 1 mm.

In accordance with implementations of the present disclosure, LIG traces can be used to provide underlying electrical interconnects between sensors, processing, energy harvesting and communications. Unpackaged chips can be integrated to maintain a thin form factor and LIG can be used to make direct contact to bond pads on the chips. This technique can also be used to integrated non-silicon electronics for more sustainable designs, such as thin film transistors, organics, and other appropriate materials used to create processing capabilities. Fabrication of the devices can be completed through a sequence of coating, aligned placement of components (processing, harvesters, communication, etc), LIG trace creation, and subsequent coating.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products (i.e., one or more modules of computer program instructions encoded on a computer readable medium for execution by, or to control the operation of, data processing apparatus). The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question (e.g., code that constitutes processor firmware, a protocol stack, a database management system, an operating system, or any appropriate combination of one or more thereof). A propagated signal is an artificially generated signal (e.g., a machine-generated electrical, optical, or electromagnetic signal) that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry (e.g., an FPGA (field programmable gate array) or an ASIC (application specific integrated circuit)).

Processors suitable for the execution of a computer program include, by way of example, both general and special purpose microprocessors, and any one or more processors of any appropriate kind of digital computer. Generally, a processor will receive instructions and data from a read only memory or a random access memory or both. Elements of a computer can include a processor for performing instructions and one or more memory devices for storing instructions and data. Generally, a computer will also include, or be operatively coupled to receive data from or transfer data to, or both, one or more mass storage devices for storing data (e.g., magnetic, magneto optical disks, or optical disks). However, a computer need not have such devices. Moreover, a computer may be embedded in another device (e.g., a mobile telephone, a personal digital assistant (PDA), a mobile audio player, a Global Positioning System (GPS) receiver). Computer readable media suitable for storing computer program instructions and data include all forms of non-volatile memory, media and memory devices, including by way of example semiconductor memory devices (e.g., EPROM, EEPROM, and flash memory devices); magnetic disks (e.g., internal hard disks or removable disks); magneto optical disks; and CD ROM and DVD-ROM disks. The processor and the memory may be supplemented by, or incorporated in, special purpose logic circuitry.

To provide for interaction with a user, implementations may be realized on a computer having a display device (e.g., a CRT (cathode ray tube), LCD (liquid crystal display) monitor) for displaying information to the user and a keyboard and a pointing device (e.g., a mouse, a trackball, a touchpad), by which the user may provide input to the computer. Other kinds of devices may be used to provide for interaction with a user as well; for example, feedback provided to the user may be any appropriate form of sensory feedback (e.g., visual feedback, auditory feedback, tactile feedback); and input from the user may be received in any appropriate form, including acoustic, speech, or tactile input.

Implementations may be realized in a computing system that includes a back end component (e.g., as a data server), a middleware component (e.g., an application server), and/or a front end component (e.g., a client computer having a graphical user interface or a Web browser, through which a user may interact with an implementation), or any appropriate combination of one or more such back end, middleware, or front end components. The components of the system may be interconnected by any appropriate form or medium of digital data communication (e.g., a communication network). Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

What is claimed is:

1. A wearable physical characteristic monitoring (PCM) device, comprising:
   a substrate comprising two or more electrical traces, the two or more electrical traces being formed as laser-induced graphene (LIG) in a starch-based material layer;
   a sensor that provides a signal responsive to physiological characteristics of a patient wearing the PCM device;
   a processing system that provides physiological characteristics data based on the signal; and
   a communications system that enables communication of the physiological characteristics data from the PCM device;
   wherein the two or more electrical traces connect one or more of the sensor, the processing system, and the communications system.

2. The wearable PCM device of claim 1, further comprising a hydrophobic layer formed on the substrate, the hydrophobic layer comprising hydrophobic graphene.

3. The wearable PCM device of claim 2, wherein the hydrophobic graphene is formed as LIG.

4. The wearable PCM device of claim 1, further comprising an adhesive layer comprising an adhesive that is free from allergens comprising colophony, balsam of Peru, 2-hydroxyethyl methacrylate, and carba mix.

5. The wearable PCM device of claim 4, wherein the adhesive is a starch-based adhesive.

6. The wearable PCM device of claim 1, wherein the communications system comprises an electrochromic display.

7. The wearable PCM device of claim 6, wherein the electrochromic display is configured to selectively display a machine-readable code that encodes at least a portion of the physiological data.

8. The wearable PCM device of claim 1, further comprising an energy harvesting unit to harvest energy to power the PCM device, the energy harvesting unit comprising one or more of an abiotic energy harvesting unit and a biotic energy harvesting unit.

9. The wearable PCM device of claim 1, wherein at least one of the two or more electrical traces is serpentine.

10. The wearable PCM device of claim 1, wherein the PCM is less than or equal to 1 mm thick.

11. The wearable PCM device of claim 1, wherein the substrate comprises a biodegradable material the is coated with the starch-based material layer, the biodegradable material comprising one or more of bamboo, lignin, chitosan, and cellulose.

12. The wearable PCM device of claim 1, wherein one or more components are one of biodegradable and recyclable.

13. A method of manufacturing a wearable physical characteristic monitoring (PCM) device, the method comprising:
   providing a substrate being composed of a starch-based material;
   forming two or more electrical traces as laser-induced graphene (LIG) in the substrate;
   mounting a set of electrical components for electrical communication between two of the two or more electrical traces: a first electrical component comprising a sensor that provides a signal responsive to physiological characteristics of a patient wearing the PCM device, and a second electrical component comprising a communication device to communicate physiological characteristics data from the PCM device;
   applying a starch-based layer to the substrate to cover the two or more electrical traces and one or more electrical components in the set of electrical components; and
   curing the starch-based layer to combine the starch-based layer and the substrate.

14. The method of claim 13, further comprising forming a hydrophobic layer on the substrate, the hydrophobic layer comprising hydrophobic graphene.

15. The method of claim 14, wherein the hydrophobic graphene-rich traces are formed as LIG.

16. The method of claim 13, further comprising applying an adhesive layer to the substrate, the adhesive layer comprising an adhesive that is free from allergens comprising colophony (rosin), balsam of Peru (3.9%), 2-hydroxyethyl methacrylate, and carba mix.

17. The method of claim 16, wherein the adhesive is a starch-based adhesive.

18. The method of claim 13, wherein the second electrical component comprises an electrochromic display.

19. The method of claim 18, wherein the electrochromic display is configured to selectively display a machine-readable code that encodes at least a portion of the physiological data.

20. The method of claim 13, wherein a third electrical component in the set of electrical components comprises an energy harvesting unit to harvest energy to power the PCM device, the energy harvesting unit comprising one or more of an abiotic energy harvesting unit and a biotic energy harvesting unit.

21. The method of claim 13, wherein at least one of the two or more electrical traces is serpentine.

22. The method of claim 13, wherein the PCM is less than or equal to 1 mm thick.

\* \* \* \* \*